United States Patent [19]
Laufer

[11] Patent Number: 6,030,365
[45] Date of Patent: Feb. 29, 2000

[54] MINIMALLY INVASIVE STERILE SURGICAL ACCESS DEVICE AND METHOD

[76] Inventor: Michael D. Laufer, 1259 El Camino Real #211, Menlo Park, Calif. 94025

[21] Appl. No.: 09/095,240

[22] Filed: Jun. 10, 1998

[51] Int. Cl.[7] .................................................. A61M 5/178
[52] U.S. Cl. .......................... 604/164; 604/96; 604/174
[58] Field of Search ............................ 604/96, 103, 104, 604/174, 176, 271, 272, 275, 164

[56] References Cited

U.S. PATENT DOCUMENTS

| | | |
|---|---|---|
| 3,709,214 | 1/1973 | Robertson . |
| 3,858,586 | 1/1975 | Lessen . |
| 3,980,078 | 9/1976 | Tominaga . |
| 4,175,545 | 11/1979 | Termanini . |
| 4,204,528 | 5/1980 | Termanini . |
| 4,224,929 | 9/1980 | Furihata . |
| 4,608,965 | 9/1986 | Anspach, Jr. et al. . |
| 4,681,093 | 7/1987 | Ono et al. . |
| 4,765,314 | 8/1988 | Kolditz et al. . |
| 4,784,133 | 11/1988 | Mackin . |
| 4,846,785 | 7/1989 | Cassou et al. . |
| 4,976,710 | 12/1990 | Mackin . |
| 5,100,419 | 3/1992 | Ehlers . |
| 5,103,804 | 4/1992 | Abele et al. . |
| 5,122,122 | 6/1992 | Allgood . |
| 5,261,889 | 11/1993 | Laine et al. ............................. 604/164 |
| 5,297,536 | 3/1994 | Wilk . |
| 5,337,730 | 8/1994 | Maguire ................................... 604/96 |
| 5,374,273 | 12/1994 | Nakao et al. . |
| 5,437,283 | 8/1995 | Ranalletta et al. . |
| 5,458,131 | 10/1995 | Wilk . |
| 5,632,717 | 5/1997 | Yoon . |
| 5,645,566 | 7/1997 | Brenneman et al. . |
| 5,685,823 | 11/1997 | Ito et al. . |
| 5,776,097 | 7/1998 | Massoud ................................. 604/96 |

*Primary Examiner*—Michael Buiz
*Assistant Examiner*—Julian W. Woo
*Attorney, Agent, or Firm*—Pennie & Edmonds LLP

[57] ABSTRACT

A device and method for creating sterile surgical access to internal body parts through a natural opening of an internal body cavity are disclosed. The device includes an elongate body member with a distal end that is inserted into the natural body opening and at least one channel that extends along the length of the body member. One of the channels, a wash channel, carries a cleansing fluid which is ejected through nozzle jets to wash a portion of a wall of the internal body cavity. The wash channel is also operatively associated with a vacuum source so that suction through the nozzle jets results in a fluid-tight connection between the distal end of the body member and the portion of the wall. A perforation channel having a deformable inflation member located between the proximal and distal ends of the channel when not inflated to maintain its sterility is inflated to extend beyond the distal end of the body member. A perforation element on the inflation member creates a hole in the portion of a wall through which a part of the deformable inflation member can extend to assume a shape having at least a section larger than the hole's diameter. Surgical instruments can be inserted in the proximal end of the body member for manipulation and visualization of the internal body parts at the distal end of the body member.

27 Claims, 7 Drawing Sheets

MINIMALLY INVASIVE STERILE SURGICAL ACCESS DEVICE AND METHOD

FIELD OF THE INVENTION

The present invention is directed to minimally invasive surgery, and in particular to a device and method for sterile access to internal body parts through a natural body opening.

BACKGROUND OF THE INVENTION

Open surgical techniques in which incisions of at least several centimeters in length are made to access the surgical area have many limitations and often lead to post-operative complications. One common problem is permanent, cosmetically unappealing scars.

Minimally invasive surgical techniques, e.g., laparoscopic surgery, reduce the overall size of scars, but do not eliminate scarring of the skin. Furthermore, whenever the peritoneum, the lining of the abdominal cavity, is cut or punctured, transforming growth factors, such as TGF-$\beta$, are released as part of the healing process. Even the small punctures associated with laparoscopy initiate the release of these substances. The growth factors induce the healing process and cause the formation of band-like connective tissue bridges known as adhesions. Adhesions can cause bowel obstructions in which the intestines twist around the adhesions and become kinked. Frequently, surgery is needed to correct the bowel obstruction and remove the adhesions. Unfortunately, the corrective surgery itself results in the release of transforming growth factors and leads to the formation of new adhesions, which can cause new bowel obstructions.

One way to avoid external scarring and the formation of adhesions would be to eliminate the need to cut the peritoneum by accessing internal body parts through a natural body opening. An example of such a technique that has been known at least for several decades is culdoscopy. During a culdoscopic procedure, an endoscopic instrument is introduced through the posterior vaginal wall to view the rectovaginal pouch and pelvic viscera. U.S. Pat. No. 4,103,680 discloses a device and method for applying elastic rings, that inter alia, can ligate fallopian tubes in connection with culdoscopic procedures.

Another natural body opening that would allow access to many internal organs in the body is the rectum. For example, an appendectomy could be conducted by gaining access to the abdominal cavity by perforating the colon. U.S. Pat. Nos. 5,458,131 and 5,297,536 disclose a method for intra-abdominal surgery in which access to the abdominal cavity is through a natural body cavity, such as the colon.

However, the most serious limitation that renders the above approach impracticable as described in the above patents are issues related to sterility. An enormous body of medical literature teaches that inadvertent perforation of the bowel could lead to serious, potentially lethal infections. An inadvertent perforation of the bowel could result in the bowel contents seeping into the abdominal cavity. This could result in sepsis. The general attitude in the surgical community is to avoid perforating the bowel because of the inability to create and maintain a sterile atmosphere in the abdominal cavity when the bowel is perforated.

Despite the significant advantages of performing surgery on internal body parts through a natural body cavity such as the colon (no scarring, no adhesions and faster patient recovery post-surgery), this procedure is currently not practiced because of the lack of a method and devices that provide a sterile path from the natural body opening through the natural body cavity to the body parts. The existing procedures or publications, such as the above-identified patents, generally do not teach a method or describe a device for maintaining a sterile route through a natural body opening such that an internal body organ could be accessed through a body cavity.

Thus, there exists a need for a device and method that would provide a sterile path for accessing internal body parts and performing surgery on those internal body parts.

SUMMARY OF THE INVENTION

The device according to the present invention includes an elongate member adapted to be inserted into a body cavity having proximal and distal ends and defining at least one lumen extending therethrough, means for perforating the body cavity wall, and means for extending through the perforated body cavity wall to create a continuation of the lumen through the body cavity wall so that the continued lumen is isolated from the body cavity. Preferably, the device further includes means for securing the distal end of said elongate member to a wall of a body cavity and means for cleansing a site on the body cavity wall to be perforated.

The means for securing can be a nozzle mounted on the distal end of the elongate member which communicates with a lumen through the elongate member though which suction may be applied such that the body cavity wall may be adhered to the nozzle by such suction. Alteratively, the means for securing comprises a concentric suction channel formed around the elongate member and lumen such that suction applied through the channel adheres the body cavity wall to the distal end of the member.

The means for perforating can be a perforation element mounted on a trocar or an inflatable member disposed in the lumen at the distal end having a perforation element mounted thereon. The inflatable member is inflatable to a position extending out of the distal end of the elongate member to expose the perforation element. Preferably, the inflatable member is configured and dimensioned to extend through the body cavity wall and is rupturable to surround edges of the perforated wall and provide the continued lumen. In another configuration, the means for extending comprises a separate tube inserted through the lumen having an inflatable seal for sealing around the perforation in the cavity wall.

In another embodiment, the device according to the present invention includes an elongate body member with at least one channel extending from the proximal end to the distal end of the elongate body member. One channel is a perforation channel having a deformable inflation member with a perforation element such that the inflation member is located between the perforation channel proximal and distal ends when not inflated and the perforation element extends beyond the distal end of the body member when inflated to create a hole in a portion of a wall of an internal body cavity through which a part of the deformable inflation member extends. In a preferred embodiment, part of the deformable inflation member extends to assume a shape having at least a section larger than a diameter of the hole.

In one embodiment, the channels also include a wash channel and a nozzle connected to a distal end of the wash channel with a plurality of jets through which streams of a cleansing fluid are ejected to wash the portion of the wall of the internal body cavity. The channels can also include a suction channel. Preferably, the suction channel is operatively associated with the nozzle so that suction from a vacuum source results in a fluid-tight connection between the distal end of the body member and the portion of the wall of the internal body cavity.

The perforation element can be a cutting tip. In a preferred embodiment, the perforation element is a sharp cutting tip that dulls with inflation of the inflation member after the hole has been created. Alternatively, the perforation element includes an electrically conductive cauterizing tip.

In another embodiment, the device according to the present invention includes a flexible sheath with a proximal end which remains outside of the natural body opening; a distal end which is inserted into the natural body opening; and a lumen which extends from the proximal end to the distal end and has a plurality of channels. The channels include a wash channel with a distal end having a nozzle with a plurality of jets through which streams of a cleansing fluid are ejected to wash a portion of a wall of the internal body cavity; a suction channel with a distal end operatively associated with the nozzle so that suction from a vacuum source results in a fluid-tight connection between the distal end of the sheath and the portion of the wall of the internal body cavity; a perforation channel having a deformable inflation member with a perforation element which is located between the perforation channel proximal and distal ends when not inflated and extends beyond the distal end of the sheath when inflated to create a hole in the portion of a wall of the internal body cavity through which a part of the deformable inflation member can extend to assume a shape having at least a section larger than a diameter of the hole; and a transport channel with a proximal end through which surgical instruments are inserted, and a distal end through which manipulation and visualization of the internal body parts are performed using the surgical instruments.

Preferably, the wash channel and suction channel are the same channel and the perforation element comprises a sharp cutting tip. Alternatively, the perforation element comprises an electrically conductive cauterizing tip.

In a preferred embodiment, the proximal end of the wash channel has a cleansing fluid connector for connection to a cleansing fluid source and a cleansing fluid controller for carrying the cleansing fluid along the wash channel at a controlled pressure. The proximal end of the suction channel has a vacuum source connector and a vacuum source controller.

The lumen can include a closing channel for accommodating a closing element which seals the hole and the distal end of the transport channel can have a piercing means for piercing through the inflation member. Preferably, the closing channel and the transport channel are the same channel.

The method according to the present invention includes the steps of inserting a distal end of a flexible sheath into the natural body opening; washing a portion of a wall of the internal body cavity with streams of a cleansing fluid ejected through a plurality of jets; and creating a hole in the portion of the wall of the internal body cavity.

Preferably, the method also includes the step of performing a surgical procedure on an internal body part through the lumen. The internal body parts can be in any internal cavity, including the abdominal and thoracic cavities.

The method can also include the steps of inflating a sterile deformable inflation member which is located in an interior space of the sheath to maintain sterility prior to inflation, and creating the hole in the portion of the wall of the internal body cavity with a perforation element located on the deformable inflation member by extending the perforation element beyond the distal end of the sheath. The deformable inflation member can be inflated so that a part of the member extends through the hole to assume a shape having at least a section larger than a diameter of the hole.

The present invention also includes the method of training a person to provide sterile access to internal body parts through a natural body opening of an internal body cavity by demonstrating or instructing performance of the above-described steps.

DESCRIPTION OF THE PREFERRED EMBODIMENTS

Figure 1:
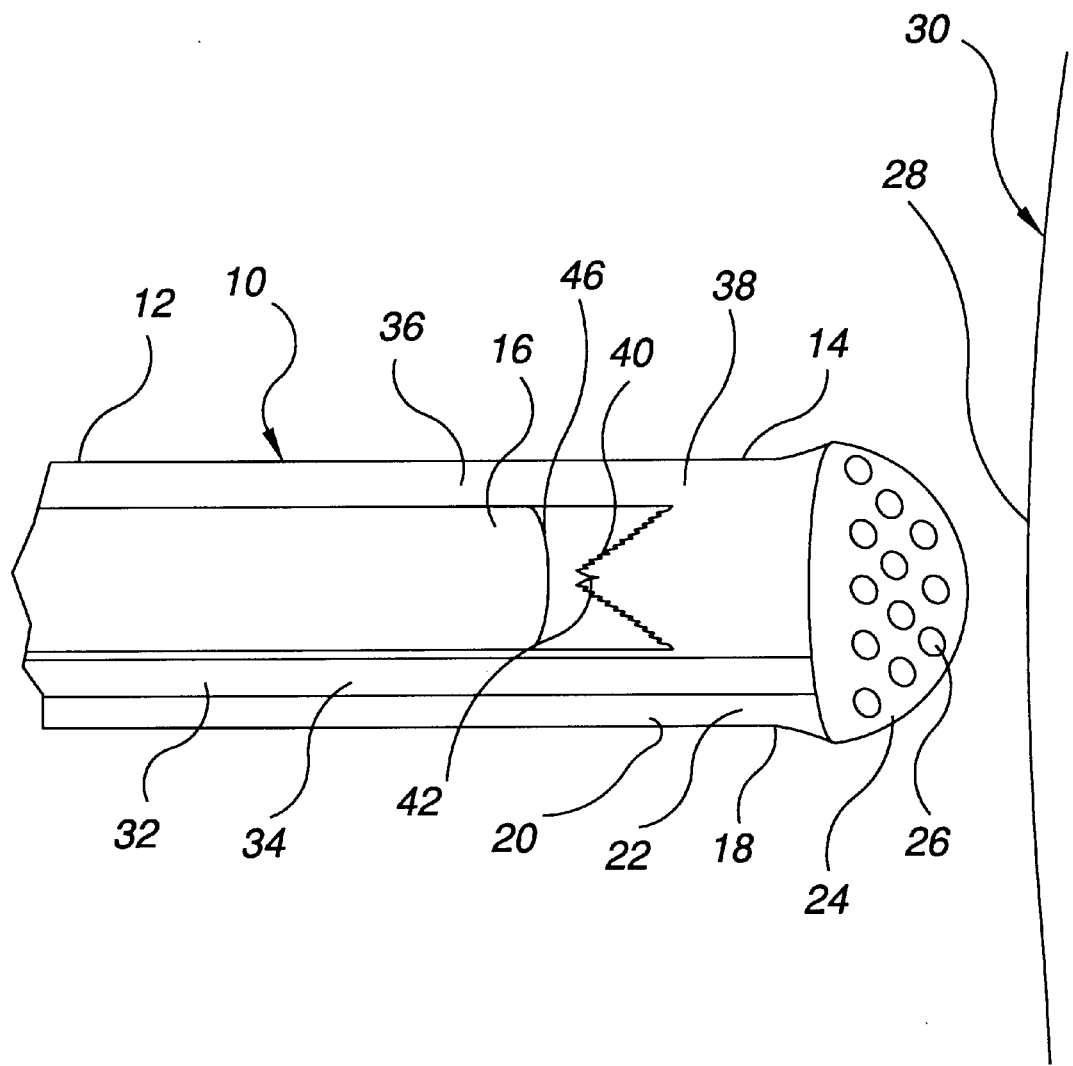
FIG. 1 is a side view of a first embodiment of a device according to the present invention with a section cut out to see a portion of the interior of the device.

FIG. 1 shows a device 10 according to the present invention. Device 10 includes elongate body 12 (which may be in the form of a flexible sheath) with a proximal end (not shown) and a distal end 14. In use, the proximal end remains outside of the natural body opening and distal end 14 is inserted into the natural body opening. A general discussion of the method of the use of the present invention will assist in understanding the details of the apparatus according to the invention.

The elongate body member is inserted into the selected natural body opening of the patient. This typically may be through the rectum to access the bowel wall for perforation and entry into the abdominal cavity in order to access internal body organs located therein. Internal body organs not in the abdominal cavity can also be accessed through the bowel wall perforation. For example, once in the abdomen, the diaphragm can be perforated as an entry to the thoracic cavity for performing a cardiac procedure. Furthermore, other natural body openings such as the vagina or the mouth, leading to natural body cavities such as the uterus or the stomach, may also be used for accessing the internal organs depending upon the procedure to be performed.

With the apparatus inserted through the rectum, an area of the bowel wall is selected and sterilized via the wash means of the present invention as described below. Once the selected area of the bowel wall has been sterilized, the distal end of the elongate body could be temporarily affixed to the sterilized wall portion by various affixing means, including suction. With the distal end of the elongate body 12 thus secured to the sterilized portion of the bowel wall, a sterile path has been created from outside the patient up to the bowel wall, the sterile portion being isolated from the other unclean areas of the bowel. At this point, the sterilized portion of the bowel wall may be perforated via a perforation means, as described below, without risk of contaminants entering the abdominal cavity from the bowel. Upon perforation, the elongate body member is secured within the hole made through the bowel wall so that a secure, sterile path has been created from outside the patient through the natural body opening into the abdominal cavity, without perforating the peritoneum. Traditional surgical procedures may then be performed via this route. It is also quite possible that, depending on the local contour of the bowel wall, the washing and cutting of the wall could be done using a side opening in the apparatus and not necessarily through the distal end of the apparatus. After the desired surgical procedures are completed, the perforation that was created in the wall of the natural body cavity is closed. Such closing could be done by suturing the hole or by any other traditional means that are suitable for closing holes in the walls of internal body cavities. It should also be understood that the invention includes training a person to provide sterile access to internal body parts through a natural body opening of an internal body cavity by demonstrating or instructing the above-described steps. With this general understanding of the method according to the present invention, the details will now be discussed.

Body 12 preferably includes lumen 16 having several channels extending from the proximal end to distal end 14 of body 12. As body 12 is inserted into the natural body opening and is moved through the internal body cavity, it is only the exterior surface 18 of body 12 that contacts the contents and the walls of the internal body cavity, and is thus exposed to the substances naturally present in the internal body cavity but may be of a contaminating nature to the internal body parts. As a result, lumen 16 remains sterile.

A wash channel 32 is one of the channels. Wash channel 32 has a proximal end (not shown) which is connected to a source of a cleansing fluid and includes a cleansing fluid controller (not shown) for carrying the cleansing fluid along the wash channel at a controlled pressure. A distal end 34 of wash channel 32 terminates at a nozzle 24. Nozzle 24 has a number of jets 26 through which streams of the cleansing fluid are ejected to wash a portion 28 of a wall 30 of the internal body cavity. The pressure at which the cleansing fluid is pumped into the wash channel and the number of jets on the nozzle 24 determine the pressure at which the cleansing fluid strikes the chosen section of the bowel wall.

Body 12 and nozzle 24 could be made of transparent material such that one can see through body 12 and nozzle 24 by placing a visualization device within lumen 16.

Another channel is a suction channel 20. In the embodiment shown in FIGS. 1–3, suction channel 20 is operatively associated with nozzle 24. A proximal end (not shown) of suction channel 20 is connected to a vacuum source and includes a vacuum source controller (not shown) for controlling the strength of the vacuum. By applying a vacuum to suction channel 20 the cleansing fluid that was injected earlier could be collected at the proximal end. Furthermore it is also possible to create a fluid-tight connection between distal end 14 of body 12 and portion 28 of wall 30 of the internal body cavity. Such a fluid-tight connection would prevent contaminants surrounding the body 12 from contaminating the cleaned surface 28 of wall 30. Preferably, wash channel 32 and suction channel 20 are combined as the same channel. The fluid-tight connection prevents the contaminants naturally present in the internal body cavity from compromising the internal body parts when a hole is made in the wall for access to the body parts.

Figure 2:
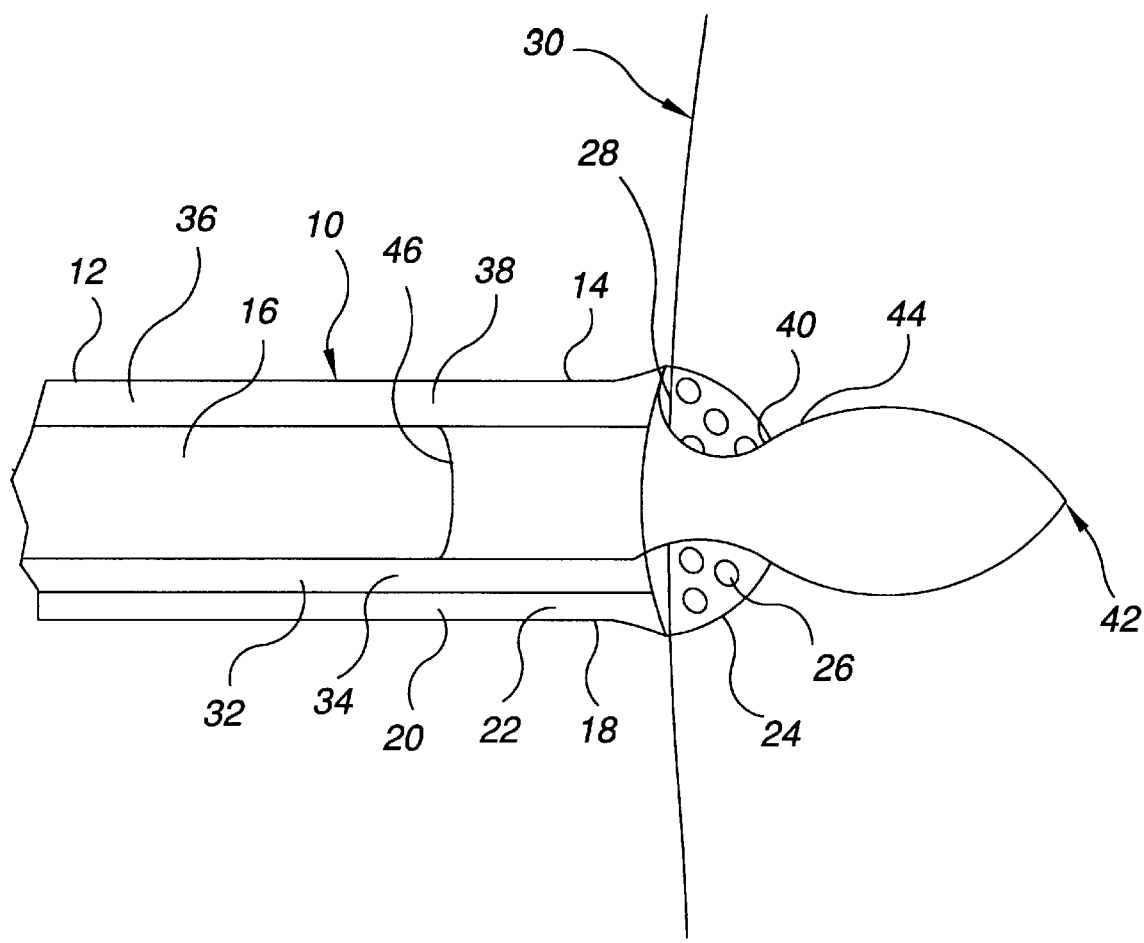
FIG. 2 is a side view of the device of FIG. 1 after a hole has been created by an inflation member in a portion of a wall of the internal body cavity.

A perforation channel 36 is a third channel. Perforation channel 36 has a proximal end (not shown) and a distal end 38 and includes a deformable inflation member 40. When not inflated, inflation member 40 is located between the proximal end and distal end 38 of perforation channel 36 so that it remains sterile. A septum 46 is located in lumen 16 behind inflation member 40. As shown in FIG. 2, when a fluid, e.g., saline, is pumped through perforation channel 36, inflation member 40 moves away from septum 46 towards nozzle 24. When inflation member 40 is inflated by the fluid, a perforation element 42 of inflation member 40 moves towards nozzle 24, extends beyond distal end 14, pierces through nozzle 24 to create a hole in portion 28 of wall 30 of the internal body cavity. Alternatively, nozzle 24 could be designed to disengage from distal end 14 at a predetermined pressure, which would eliminate the need for perforation element 42 having to pierce through nozzle 24. Perforation element 42 could be a sharp cutting tip. Alternatively, perforation element 42 is a cauterizing tip that uses electricity to heat the wall and create the hole. The wires needed for the cauterizing tip can run through perforation channel 36 or can be carried in a separate channel. As inflation continues, a part 44 of inflation member 40 extends into the hole and assumes a shape having at least one section larger than the diameter of the hole. This prevents part 44 from pulling out of the hole and seals the hole to preclude contamination of the internal body parts.

Figure 3:
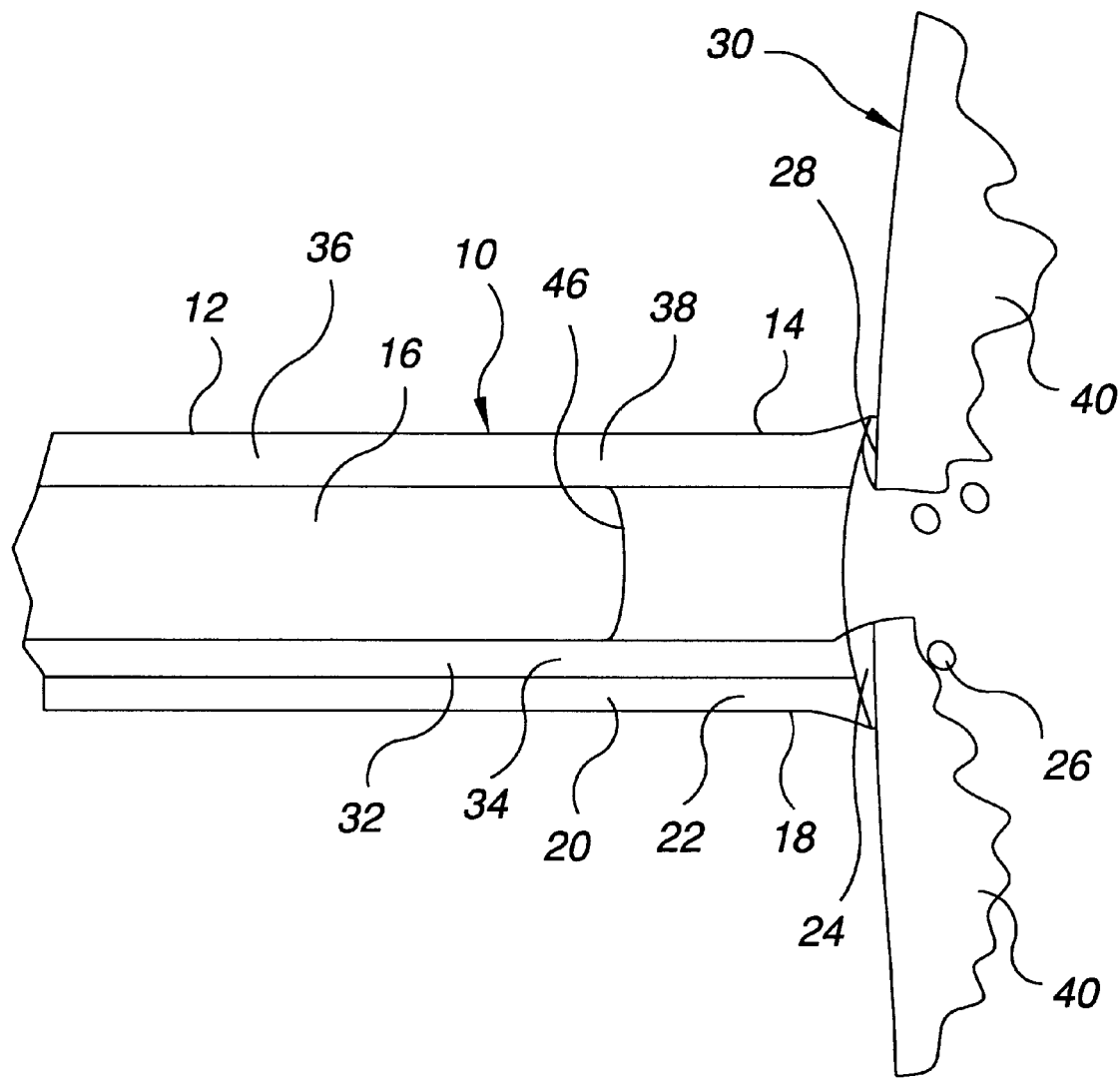
FIG. 3 is a side view of the device of FIG. 1 after the inflation member has been deflated.

Surgical instruments and visualization systems can be inserted into the proximal end of body 12 and used through distal end 14 of body 12 to visualize and manipulate the internal body parts. There are a number of ways in which this can be accomplished. As shown in FIG. 3, lumen 16 is a path through which the instruments could be inserted. Septum 46 and inflation member 40 are punctured using an incising instrument or some other means. The deflated inflation member 40 rests against a surface of wall 30 to keep the fluid-tight connection between distal end 14 of body 12 and wall 30.

Septum 46 can also be a one-way valve. In this case, perforation channel 36 becomes unnecessary and inflation member 40 could be inflated by pumping fluid into lumen 16 through septum 46.

Figure 4:
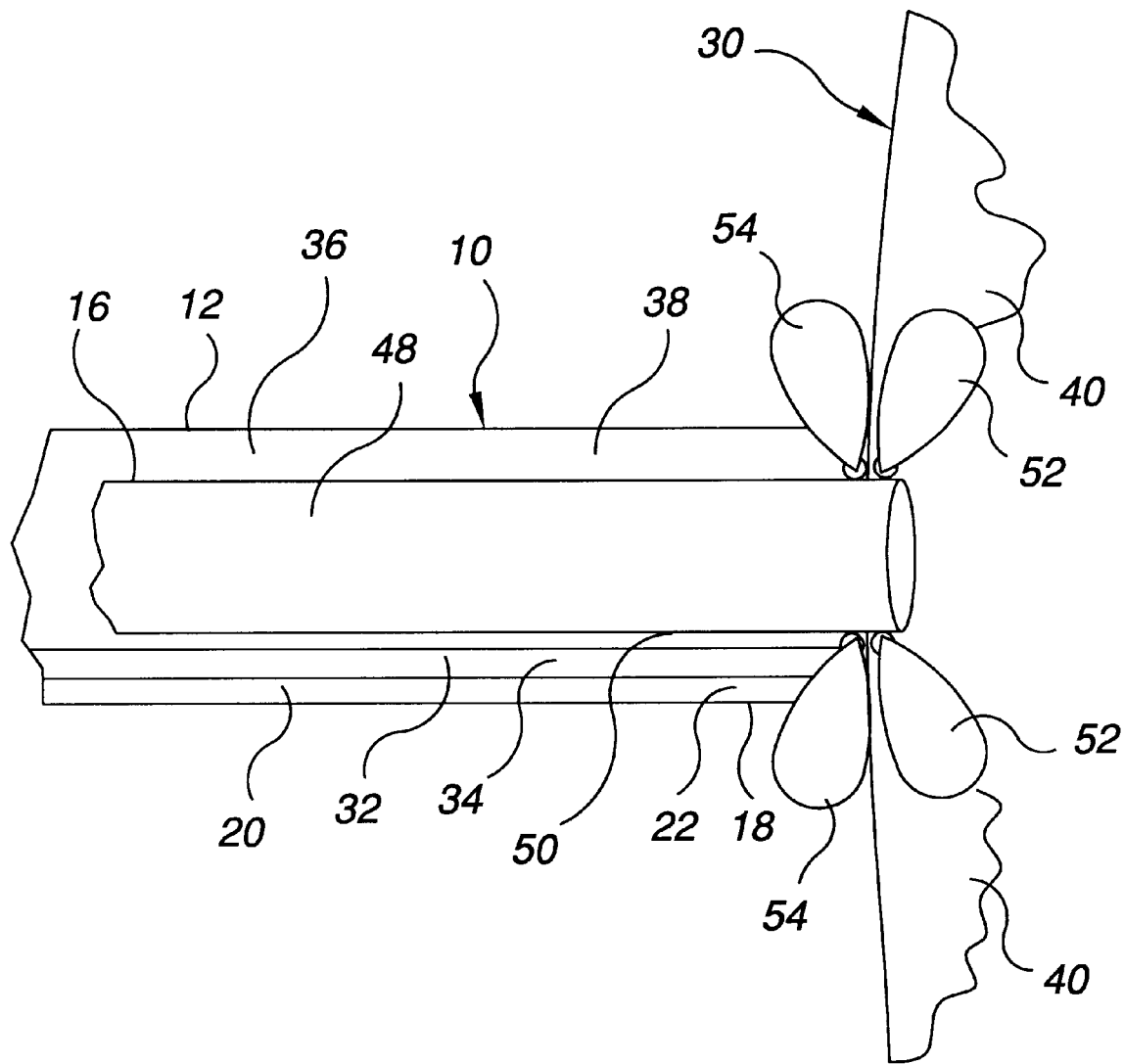
FIG. 4 is a side view of the device of FIG. 1 with a semi-rigid tube inserted through the hole.

Alternatively, once a sterile path has been established and inflation member 40 has penetrated portion 28, as shown in FIG. 4, a semi-rigid tube 48 with a proximal end (not shown) and a distal end 50 is inserted through sheath 12. Tube 48 has two inflatable elements 52 and 54. Inflatable element 52 is positioned on the inside of wall 30 and inflatable element 54 is positioned on the outside of wall 30. These inflatable elements are connected to an inflation source at the proximal end. Once inflatable elements 52 and 54 sandwich wall 30 they can be inflated to hold tube 48 in place.

Figure 5:
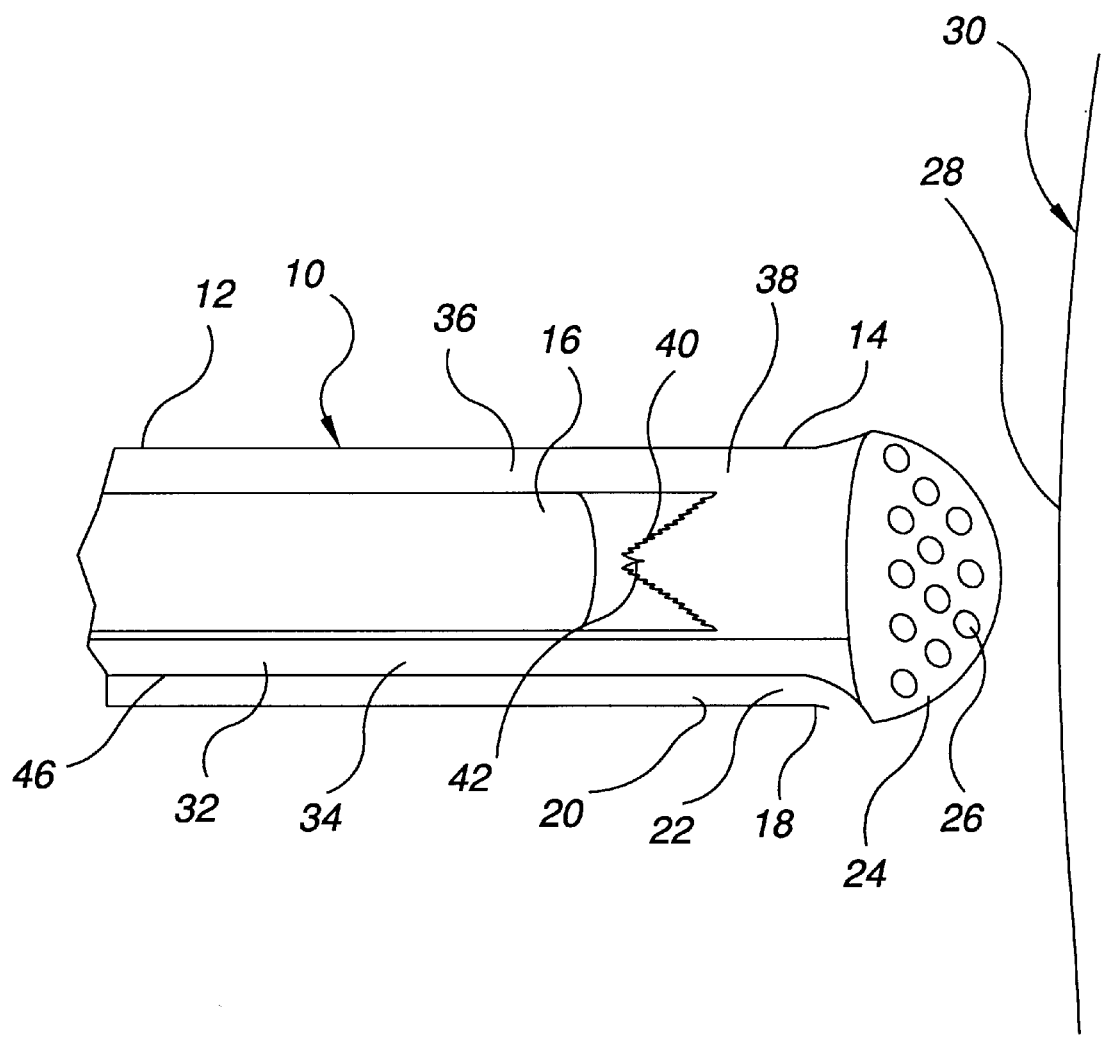
FIG. 5 is a side view of another embodiment of a device according to the present invention with a section cut out to see a portion of the interior of the device.

Another embodiment is shown in FIG. 5. Here, distal end 22 of suction channel 20 is not connected to nozzle 24. Hence, when vacuum is applied to suction channel 20 from the proximal end, suction channel 20 sucks fluids from the area surrounding device 10. This allows for simultaneous cleansing by injecting cleansing fluid through wash channel 32 and suctioning through suction channel 20. Furthermore, having a suction channel outside sterile lumen 16 allows placing a visualization system that would aid in placing body 12 in the appropriate location in the body cavity.

Figure 6:
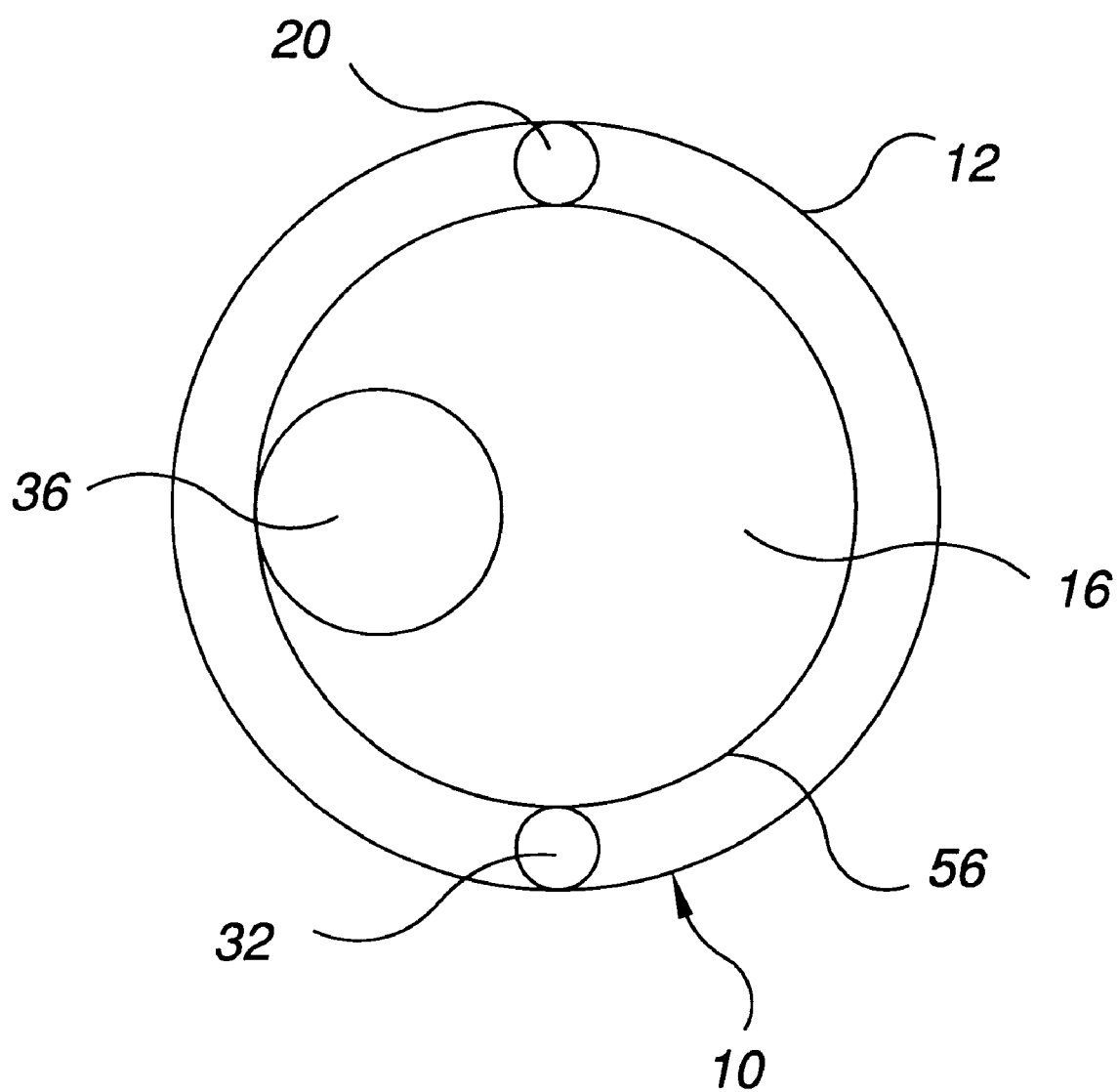
FIG. 6 is an end view of a cross section of a third embodiment of a device according to the present invention in which the nozzle has been removed from the device.

In yet another embodiment as shown in FIG. 6, perforation channel 36 is housed inside lumen 16. Wash channel 32 is a lumen attached to an external surface 56 of lumen 16 with distal end 34 affixed to nozzle 24. Suction channel 20 is also attached to external surface 56 of lumen 16. Distal end 22 of suction channel 20 is open and is not attached to nozzle 24.

Figure 7:
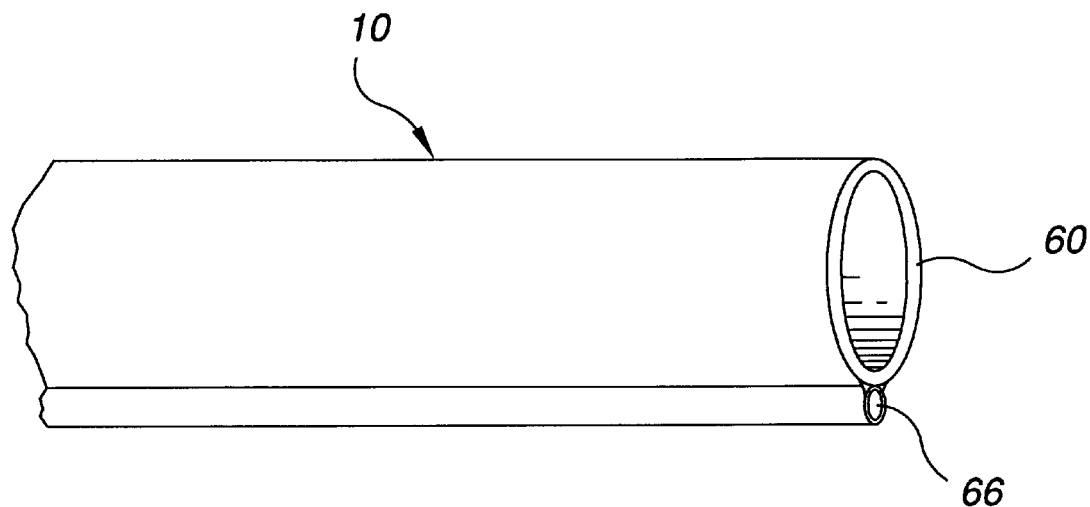
FIG. 7 is a perspective view of a distal end of a further alternative embodiment of the present invention.
Figure 8:
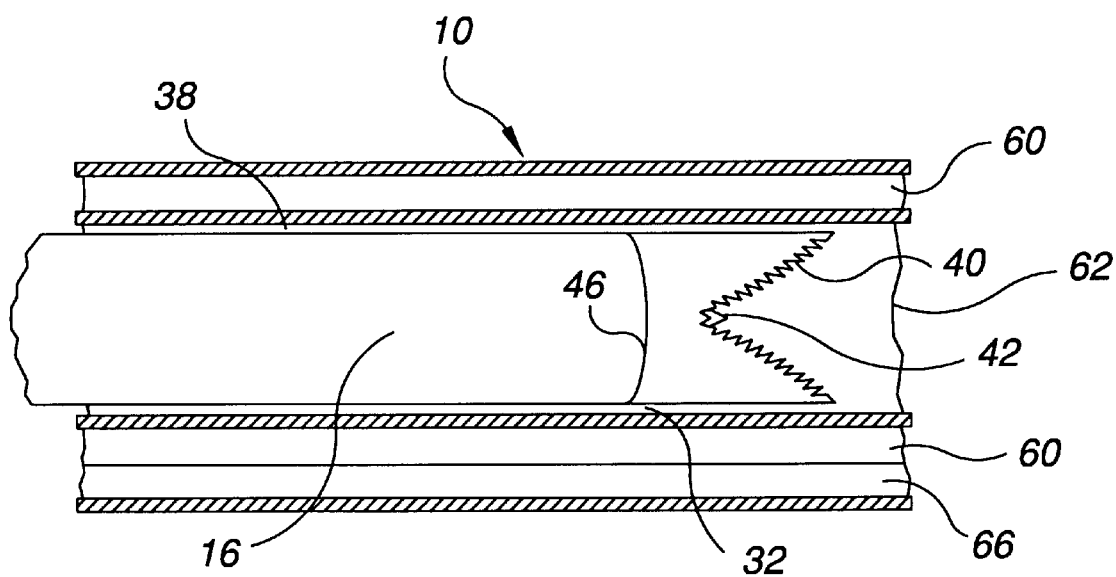
FIG. 8 is a transverse cross-section of the embodiment of the present invention shown in FIG. 7.

In a further alternative embodiment of the present invention, illustrated in FIGS. 7 and 8, a separate, concentric suction channel 60 is provided to facilitate adherence of the device to the bodywall to be perforated. In this embodiment, the distal opening of the device, which contains inflation member 40 and perforation element 42 is covered by thin, porous and pierceable membrane 62. Membrane 62 helps perforation element 42 remain sterile when the device is handled or inserted through the natural body opening. Membrane 62 is also sufficiently porous so that wash solution may freely flow through the membrane in order to clean the subject area of the bodywall. Optionally, membrane 62 may be omitted so long as the perforation element is sufficiently secured within lumen 16. In another alternative, inflation member 40 can be eliminated by having perforation element 42 separately mounted on a trocar.

Wash channel 32 is illustrated as a single channel, however, it may also be provided as multiple channels so that simultaneous irrigation and suction may be applied to more thoroughly wash the target site. Also provided in this alternative embodiment is an optional exterior suction/irrigation/visualization lumen 66. In utilizing this embodiment of the invention, washing may occur as distal end of the device approaches the body cavity wall. Alternatively, or in addition to such washing, concentric suction channel 60 may be used to adhere the distal end of the device to the wall, while permitting washing and sterilization to continue through channel 32. In this manner, once the device is adhered to the body cavity wall via concentric suction channel 60, washing may continue and be completed via channel 32 without risk of compromising the sterile surface.

While it is apparent that the illustrative embodiments of the invention herein disclosed fulfil the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. A surgical device, comprising:
   an elongate member adapted to be inserted into a body cavity, having proximal and distal ends and defining at least one lumen extending therethrough;
   means for perforating the body cavity wall;
   means for extending through the perforated body cavity wall to create a continuation of said lumen through the body cavity wall, said continued lumen being isolated from the body cavity; and
   means for securing the distal end of said elongate member to a wall of a body cavity,
      wherein said means for securing comprises a nozzle mounted on the distal end of said elongate member, said nozzle communicating with a lumen through said elongate member though which suction may be applied such that the body cavity wall may be adhered to the nozzle by such suction.

2. A surgical device, comprising:
   an elongate member adapted to be inserted into a body cavity, having proximal and distal ends and defining at least one lumen extending therethrough;
   means for perforating the body cavity wall;
   means for extending through the perforated body cavity wall to create a continuation of said lumen through the body cavity wall, said continued lumen being isolated from the body cavity; and
   means for securing the distal end of said elongate member to a wall of a body cavity,
      wherein said means for securing comprises a concentric suction channel formed around said elongate member and lumen, such that suction applied through said channel adheres the body cavity wall to the distal end of said member.

3. A surgical device, comprising:
   an elongate member adapted to be inserted into a body cavity, having proximal and distal ends and defining at least one lumen extending therethrough;
   means for perforating the body cavity wall; and
   means for extending through the perforated body cavity wall to create a continuation of said lumen through the body cavity wall, said continued lumen being isolated from the body cavity,
      wherein said means for perforating comprises an inflatable member disposed in said lumen at the distal end, said inflatable member having a perforation element mounted thereon, said inflatable member inflatable to a position extending out of the distal end of the elongate member to expose said perforation element.

4. The device according to claim 3, wherein said means for extending comprises said inflatable member being configured and dimensioned to extend through the body cavity wall, said inflatable member being rupturable to surround edges of the perforated wall and provide said continued lumen.

5. The device according to claim 3, wherein said means for extending comprises a separate tube inserted through said lumen having an inflatable seal for sealing around the perforation in the cavity wall.

6. A surgical device, comprising:
   an elongate member adapted to be inserted into a body cavity, having proximal and distal ends and defining at least one lumen extending therethrough;
   means for perforating the body cavity wall; and
   means for extending through the perforated body cavity wall to create a continuation of said lumen through the body cavity wall, said continued lumen being isolated from the body cavity,
      wherein said means for perforating comprises a perforation element mounted on a trocar.

7. A device for providing sterile access to internal body parts through a natural body opening of an internal body cavity, comprising:
   an elongate body member with a proximal end, a distal end, and defining at least one channel extending from the proximal end to the distal end; and
   a deformable inflation member mounted in the distal end of said body member with a perforation element formed thereon, said inflation member communicating with said at least one channel for inflation thereof from a first, deflated position disposed within said body member wherein said perforation element is sheathed and a second, inflated position with said perforation element extending beyond the distal end of the body member such that the perforation element may perforate an internal body wall and the inflation member may extend through said perforation.

8. The device of claim 7 wherein part of the deformable inflation member extends to assume a shape having at least a section larger than the perforation formed in the internal body wall by said perforation element.

9. The device of claim 7 wherein the at least one channel further includes:
   a wash channel with a proximal end and a distal end; and
   a nozzle at the distal end of the wash channel with a plurality of jets through which streams of a cleansing fluid are ejected to wash the portion of the wall of the internal body cavity.

10. The device of claim 9 wherein the at least one channel further includes a suction channel.

11. The device of claim 10 wherein the suction channel is operatively associated with the nozzle so that suction from a vacuum source results in a fluid-tight connection between the distal end of the body member and the portion of the wall of the internal body cavity.

12. The device of claim 7 wherein the perforation element comprises a cutting tip.

13. The device of claim 7 wherein the perforation element comprises a sharp cutting tip that dulls with continued inflation of the inflation member after the hole has been created.

14. The device of claim 7 wherein the perforation element comprises an electrically conductive cauterizing tip.

15. A device for providing sterile access to internal body parts, through a natural body opening of an internal body cavity, the device comprising:
   a flexible sheath with a proximal end adapted to remain outside of the natural body opening, a distal end adapted to be insertable into the natural body opening, and a lumen which extends from the proximal end to the distal end and has a plurality of channels, said plurality of channels including:
      a wash channel with a proximal end and a distal end having a nozzle with a plurality of jets through which streams of a cleansing fluid are ejected to wash a portion of a wall of the internal body cavity;
      a suction channel with a proximal end and a distal end operatively associated with the nozzle so that suction from a vacuum source results in a fluid-tight connection between the distal end of the sheath and the portion of the wall of the internal body cavity;
      a perforation channel with a proximal end and a distal end, said perforation channel including a deformable inflation member with a perforation element, said inflation member located between the perforation channel proximal and distal ends when not inflated and said perforation element extending beyond the distal end of the sheath when inflated to create a hole in the portion of a wall of the internal body cavity through which a part of the deformable inflation member can extend to assume a shape having at least a section larger than a diameter of the hole; and
      a transport channel with a proximal end through which surgical instruments are inserted, and a distal end through which manipulation and visualization of the internal body parts are performed using the surgical instruments.

16. The device of claim 15 wherein the wash channel and suction channel are the same channel.

17. The device of claim 15 wherein the perforation element comprises a sharp cutting tip.

18. The device of claim 15 wherein the perforation element comprises an electrically conductive cauterizing tip.

19. The device of claim 15 wherein the proximal end of the wash channel has a cleansing fluid connector for connection to a cleansing fluid source and a cleansing fluid controller for carrying the cleansing fluid along the wash channel at a controlled pressure.

20. The device of claim 15 wherein the proximal end of the suction channel has a vacuum source connector and a vacuum source controller.

21. The device of claim 15 wherein the lumen includes a closing channel for accommodating a closing element which seals the hole.

22. The device of claim 15 wherein the distal end of the transport channel has a piercing means for piercing through the inflation member.

23. The device of claim 21 wherein the closing channel and the transport channel are the same channel.

24. A method for providing sterile access to internal body parts through a natural body opening of an internal body cavity comprising the steps of:
   inserting a distal end of a flexible sheath into the natural body opening, wherein said sheath defines at least one sterile internal lumen;
   washing a portion of a wall of the internal body cavity;
   creating a hole in the washed portion of the wall of the internal body cavity;
   extending the lumen though said hole while maintaining sterility within the lumen;
   inflating a sterile deformable inflation member, said inflation member located in an interior space of the sheath to maintain sterility prior to inflation; and
   creating the hole in the portion of the wall of the internal body cavity with a perforation element located on the deformable inflation member by extending the perforation element beyond the distal end of the sheath.

25. The method of claim 24 further comprising the step of:
   inflating the deformable inflation member so that a part of said member extends through the hole to assume a shape having at least a section larger than a diameter of the hole.

26. A method for providing sterile access to internal body parts through a natural body opening of an internal body cavity, comprising:
   inserting a distal end of an elongate member into the natural body opening, wherein said member defines at least one sterile lumen therethrough;
   washing a target site on a wall of the internal body cavity;
   securing the distal end of the elongate member to the target site on the wall;
   creating a hole through the cavity wall at the target site; and
   extending the lumen though said hole while maintaining sterility within the lumen.

27. The method according to claim 26, wherein said washing continues after said securing.

* * * * *